US010724511B2

(12) United States Patent
Rowe et al.

(10) Patent No.: US 10,724,511 B2
(45) Date of Patent: Jul. 28, 2020

(54) PRESSURE ADJUSTMENT APPARATUS AND METHOD

(71) Applicant: TELEFLEX MEDICAL INCORPORATED, Research Triangle Park, NC (US)

(72) Inventors: David Troy Rowe, Sinking Spring, PA (US); John C. Victor, Kunkletown, PA (US); Jeffrey Vitullo, Pottstown, PA (US); Rodney Wilmer Denlinger, Lancaster, PA (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 617 days.

(21) Appl. No.: 14/209,985

(22) Filed: Mar. 13, 2014

(65) Prior Publication Data
US 2014/0271255 A1 Sep. 18, 2014

Related U.S. Application Data

(60) Provisional application No. 61/784,976, filed on Mar. 14, 2013.

(51) Int. Cl.
F04B 39/00 (2006.01)
F04B 39/10 (2006.01)
(Continued)

(52) U.S. Cl.
CPC ........... F04B 39/10 (2013.01); A61M 16/044 (2013.01); F04B 39/08 (2013.01); F04B 53/10 (2013.01); F04B 53/109 (2013.01)

(58) Field of Classification Search
CPC .......... F04B 39/08; F04B 39/10; F04B 53/10; F04B 53/109; A61M 16/044
(Continued)

(56) References Cited

U.S. PATENT DOCUMENTS 2,385,102 A * 9/1945 Parker ................... F02N 99/006
  137/565.12
2,961,003 A * 11/1960 Shafer ................... F04B 7/0007
  137/625.23

(Continued)

FOREIGN PATENT DOCUMENTS

CN 202459712 U 10/2012
DE 3322068 A1 12/1984
(Continued)

Primary Examiner — Christopher S Bobish
(74) Attorney, Agent, or Firm — Baker & Hostetler LLP

(57) ABSTRACT

A pressure adjustment apparatus including a pump, a selector valve coupled to the pump, and a chamber in selective fluid communication with the pump through the selector valve is disclosed. The pump includes a pump body that defines a variable volume therein, the pump body further defining a first aperture and a second aperture therethrough. The selector valve includes a first check valve disposed in a first fluid channel of a plurality of fluid channels, the first check valve being oriented to permit flow through the first fluid channel only in a first flow direction, the first flow direction being a flow direction out of the variable volume, and a second check valve disposed in a second fluid channel of the plurality of fluid channels, the second check valve being oriented to permit flow through the second fluid channel only in a second flow direction.

20 Claims, 8 Drawing Sheets

(51) Int. Cl.
*F04B 53/10* (2006.01)
*A61M 16/04* (2006.01)
*F04B 39/08* (2006.01)

(58) Field of Classification Search
USPC ............ 417/442, 502, 503, 519; 137/625.15; 251/344
See application file for complete search history.

(56) References Cited

U.S. PATENT DOCUMENTS

| | | | | |
|---|---|---|---|---|
| 3,405,601 A | * | 10/1968 | Clarke | F15B 11/072 137/212 |
| 3,794,043 A | * | 2/1974 | McGinnis | A61M 16/044 128/207.15 |
| 3,837,360 A | * | 9/1974 | Bubula | F16K 11/0743 137/625.11 |
| 3,918,437 A | * | 11/1975 | Saba | A61B 5/0235 251/147 |
| 4,195,631 A | * | 4/1980 | Baucom | A61M 1/3693 137/625.15 |
| 4,407,275 A | * | 10/1983 | Schroeder | A61F 5/41 600/38 |
| 4,727,887 A | | 3/1988 | Haber | |
| 4,825,862 A | | 5/1989 | Sato et al. | |
| 5,156,538 A | * | 10/1992 | Lee | F04B 9/14 417/236 |
| 5,328,456 A | * | 7/1994 | Horiguchi | A61M 1/0058 604/22 |
| 5,489,196 A | * | 2/1996 | Lee | F04B 9/14 417/239 |
| 5,992,459 A | * | 11/1999 | Sugita | F16K 11/0743 137/625.43 |
| 6,422,832 B1 | * | 7/2002 | Wang | F04B 33/00 417/239 |
| 6,591,619 B2 | * | 7/2003 | Kaneko | F16K 11/074 137/625.31 |
| 6,955,531 B2 | * | 10/2005 | Wu | F04B 33/00 137/231 |
| 7,040,347 B2 | * | 5/2006 | Wang | A45B 19/02 137/565.12 |
| 7,204,271 B2 | * | 4/2007 | Kasai | F16K 11/0743 137/625.46 |
| 7,207,780 B2 | | 4/2007 | Bach | |
| 7,484,944 B2 | | 2/2009 | Kasmer | |
| 7,753,885 B2 | | 7/2010 | Duchon et al. | |
| 8,721,589 B1 | * | 5/2014 | Stanhope | A61M 16/044 604/96.01 |
| 8,800,167 B2 | * | 8/2014 | Doyle | A43B 13/203 36/153 |
| 2003/0183285 A1 | * | 10/2003 | Yang | F16K 15/147 137/625.17 |
| 2005/0135952 A1 | | 6/2005 | Bach | |
| 2009/0229605 A1 | | 9/2009 | Efrati | |
| 2010/0179488 A1 | | 7/2010 | Spiegel et al. | |
| 2010/0249587 A1 | | 9/2010 | Duchon et al. | |
| 2011/0015738 A1 | | 1/2011 | Vaingast et al. | |
| 2011/0253145 A1 | | 10/2011 | Calderoni et al. | |
| 2012/0204884 A1 | | 8/2012 | Howard | |
| 2012/0241469 A1 | | 9/2012 | Takeishi et al. | |
| 2014/0271255 A1 | * | 9/2014 | Rowe | F04B 39/10 417/53 |

FOREIGN PATENT DOCUMENTS

| | | |
|---|---|---|
| JP | 3-217671 A | 9/1991 |
| JP | 2001-61965 A | 3/2001 |
| JP | 2002-219175 A | 8/2002 |
| JP | 2012-241714 A | 12/2012 |
| WO | 2011/127385 A1 | 10/2011 |

* cited by examiner

PRESSURE ADJUSTMENT APPARATUS AND METHOD

CROSS REFERENCE TO RELATED APPLICATION

This application claims the benefit of U.S. Provisional Application No. 61/784,976, filed on Mar. 14, 2013, the disclosure of which is hereby incorporated by reference in its entirety.

FIELD OF THE INVENTION

The present invention relates generally to pressure adjustment apparatus and methods of using the same. More particularly, the present invention relates to apparatus and methods suitable for inflating and deflating an inflatable cuff of an endotracheal tube.

BACKGROUND OF THE INVENTION

Inflatable cuffs have been proposed for applying occlusive pressure to a flow lumen of a patient's body, or for sealing between a medical instrument and a flow lumen of a patient's body. For example, an endotracheal tube may include an inflatable cuff that conforms to the contours of a patient's trachea when inserted into the trachea and inflated to seal a gap between the endotracheal tube and the trachea. Further, syringes have been proposed for inflating an inflatable cuff.

U.S. Pat. No. 4,727,887 (hereinafter "the '887 patent") describes an artificial sphincter with an occlusion cuff for applying occlusive pressure to a flow lumen of a patient's body (e.g., a urethra). The '887 patent further proposes a combination hypodermic manometer including a piston assembly, which is adapted for reciprocal movement through a fluid-filled sleeve. As the piston assembly of the '887 patent is moved through the sleeve, a bellows is compressed, thereby changing a height of fluid within a manometer fluidly coupled to the bellows.

However, to inflate some occlusion cuffs with less than one full stroke of the hypodermic manometer, the sleeve may require an unduly large internal volume. Further, large sleeve cross sectional areas, which promote the ability to inflate the occlusion cuff with less than one full stroke, impair the ability of the operator to make fine adjustments to the fluid pressure within the occlusion cuff, because small changes in piston position may result in unduly large changes in cuff pressure. Moreover, if the fluid necessary to inflate the occlusion cuff exceeds the volume within the sleeve, then the hypodermic manometer may need to be uncoupled from the occlusion cuff to refill the sleeve before additional fluid can be delivered to the occlusion cuff by subsequent strokes of the piston within the sleeve, thereby impairing the user's ability to make quick and precise changes to the occlusion cuff pressure.

In addition, pressure indicating accuracy of the hypodermic manometer of the '887 patent may depend upon orientation of the manometer with respect to gravity, making it difficult to use with accuracy in practice. Further still, a rupture or leak of the bellows poses the risk of mixing the manometer fluid with the fluid in contact with the occlusive cuff.

Accordingly, methods and apparatus that enable quick and precise adjustments of a pressure within an inflatable cuff, and which enable cuff pressure monitoring that is insensitive to the orientation of the apparatus, are desired.

SUMMARY OF THE INVENTION

One aspect of the present invention advantageously provides a pressure adjustment apparatus, comprising a pump, a selector valve coupled to the pump, and a chamber in selective fluid communication with the pump through the selector valve. The pump includes a pump body that defines a variable volume therein, the pump body further defines a first aperture and a second aperture therethrough, such that the first aperture and the second aperture of the pump body are in fluid communication with the variable volume. The selector valve defines a plurality of fluid channels therethrough. The selector valve includes a first check valve disposed in a first fluid channel of the plurality of fluid channels, the first check valve being oriented to permit flow through the first fluid channel only in a first flow direction, the first flow direction being a flow direction out of the variable volume, and a third check valve disposed in a third fluid channel of the plurality of fluid channels, the third check valve being oriented to permit flow through the third fluid channel only in a second flow direction, the second flow direction being a flow direction into the variable volume. When the selector valve is oriented in a first position or orientation relative to the pump, the first aperture of the pump body is in fluid communication with the first fluid channel of the selector valve, thereby permitting a flow from the variable volume of the pump into the chamber through the first fluid channel. When the selector valve is oriented in a second position relative to the pump, the first aperture of the pump body is in fluid communication with the third fluid channel of the selector valve, thereby permitting a flow from the chamber into the variable volume of the pump through the third fluid channel.

Another aspect of the present invention advantageously provides an inflatable cuff system, comprising a tube defining a lumen therein, a pump, a selector valve coupled to the pump and the tube, and an inflatable cuff in fluid communication with the pump via the selector valve and the lumen. The pump includes a pump body that defines a variable volume therein, the pump body further defines a first aperture and a second aperture therethrough, such that the first aperture and the second aperture of the pump body are in fluid communication with the variable volume. The selector valve defines a plurality of fluid channels therethrough. The selector valve includes a first check valve disposed in a first fluid channel of the plurality of fluid channels, the first check valve being oriented to permit flow through the first fluid channel only in a first flow direction, the first flow direction being a flow direction out of the variable volume, and a third check valve disposed in a third fluid channel of the plurality of fluid channels, the third check valve being oriented to permit flow through the third fluid channel only in a second flow direction, the second flow direction being a flow direction into the variable volume. When the selector valve is oriented in a first position relative to the pump, the first aperture of the pump body is in fluid communication with the first fluid channel of the selector valve, thereby permitting a flow from the variable volume of the pump into the inflatable cuff through the first fluid channel. When the selector valve is oriented in a second position relative to the pump, the first aperture of the pump body is in fluid communication with the third fluid channel of the selector valve, thereby permitting a flow from the inflatable cuff into the variable volume of the pump through the third fluid channel.

Yet another aspect of the present invention advantageously provides a method of adjusting a pressure in a system, the system including a pump fluidly coupled to a chamber through a selector valve, the pump having a pump body that defines a variable volume therein, the pump body further defining a first aperture and a second aperture therethrough, the first aperture and the second aperture being in fluid communication with the variable volume, the method comprising orienting the selector valve to a first position of a plurality of positions relative to the pump, flowing a first fluid from the variable volume into a first flow channel of the selector valve via a first check valve by decreasing a volume of the variable volume, and flowing a second fluid from a fluid source into a second flow channel of the selector valve via a second check valve by increasing the volume of the variable volume, wherein the second flow channel is separate from the first flow channel.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, the phraseology and terminology employed herein, as well as the Abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. Therefore, the claims shall be regarded as including such equivalent constructions insofar as they do not depart from the spirit and scope of the present invention.

DETAILED DESCRIPTION

Figure 1:
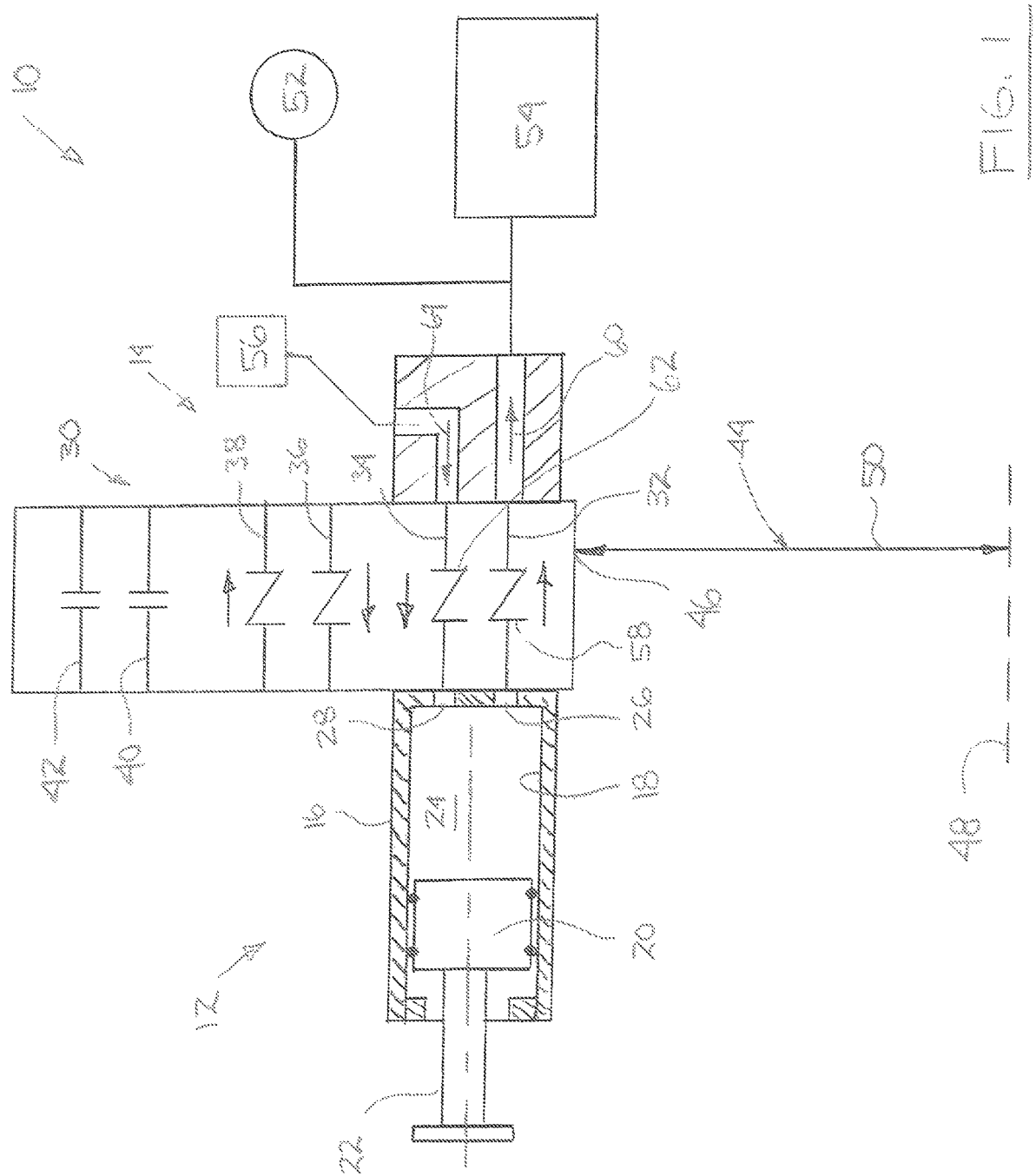
FIG. 1 presents a schematic view of a pressure adjustment apparatus according to an embodiment of the present invention.

The invention will now be described with reference to the drawing figures, in which like reference numerals refer to like parts throughout. An embodiment in accordance with the present invention provides a pressure adjustment apparatus suitable for adjusting and monitoring a pressure within an inflatable cuff.

FIG. 1 presents a schematic view of a pressure adjustment apparatus 10 according to an embodiment of the present invention. The pressure adjustment apparatus 10 includes a pump 12 coupled to a selector valve 14. The pump 12 includes a pump body 16 that defines a pump bore 18 therein. A piston 20 is movably disposed within the pump bore 18, and may include a piston stem 22 that projects beyond the pump body 16. The piston stem 22 enables a user to translate the piston 20 within the pump bore 18 by applying a force to the piston stem 22.

The pump bore 18 and the piston 20 define a variable volume 24 therebetween. Further, the pump body 16 defines a first aperture 26 and a second aperture 28 therethrough, such that the variable volume 24 is in fluid communication with both the first aperture 26 and the second aperture 28 of the pump body 16.

The selector valve 14 defines a plurality of fluid channels 30 therein. In one embodiment of the present invention the selector valve 14 defines six fluid channels therein, including: a first fluid channel 32, a second fluid channel 34, a third fluid channel 36, a fourth fluid channel 38, a fifth fluid channel 40, and a sixth fluid channel 42. However, it will be appreciated that the plurality of fluid channels 30 could include any number of fluid channels greater than one.

The selector valve 14 is configured to move relative to the pump 12. The relative motion between the selector valve 14 and the pump 12 may include translation, rotation, or combinations thereof. The orientation of the selector valve 14 may be measured or identified by a variable distance 44 between a point 46 on the selector valve 14 and a reference position 48. In one aspect of the present invention the reference position 48 is disposed on the pump 12. However, it will be appreciated that the reference position 48 could be defined in any reference frame that accommodates relative motion with respect to the selector valve 14. Further, it will be appreciated that the variable distance 44 could be defined in terms of a translational distance or a rotational distance depending on the nature of the relative motion between the selector valve 14 and the pump 12.

In one embodiment of the present invention, the variable distance 44 between the selector valve 14 and the reference position 48 defines a first position or orientation 50 of the selector valve 14. When the selector valve 14 is oriented in the first position or orientation 50, the first aperture 26 of the pump body 16 is in fluid communication with a chamber 52, a pressure indicator 54, or combinations thereof, via the first fluid channel 32; and the second aperture 28 of the pump body 16 is in fluid communication with a fluid supply 56 via the second fluid channel 34. It will be appreciated that the fluid supply 56 could be a fluid reservoir or an ambient environment of the pressure adjustment apparatus 10.

According to an aspect of the present invention, a first check valve 58 is disposed in the first fluid channel 32 of the selector valve 14. The first check valve 58 may be oriented to permit flow through the first fluid channel 32 only in a flow direction 60 out of the variable volume 24 of the pump 12. Further, a second check valve 62 may be disposed in the second fluid channel 34 of the selector valve 14. The second check valve 62 may be oriented to permit flow through the second fluid channel 34 only in a flow direction 64 into the variable volume 24 of the pump 12. According to another aspect of the invention, when the selector valve is located in the first position or orientation 50, the variable volume 24 of the pump is not in fluid communication with any of the third fluid channel 36, the fourth fluid channel 38, the fifth fluid channel 40, or the sixth fluid channel 42.

When the selector valve 14 is oriented in the first position or orientation 50, decreasing the size of the variable volume 24 of the pump 12 compresses fluid therein and effects a flow of fluid from the variable volume 24 into the first check valve 58 through the first fluid channel 32. Optionally, the fluid flowing through the first fluid channel may increase a pressure within the chamber 52, the pressure indicator 54, or combinations thereof. It will be appreciated that the second check valve 62 will not permit flow from the variable volume 24 to the fluid supply 56 because of the orientation of the second check valve 62.

Further, when the selector valve 14 is oriented in the first position or orientation 50, increasing the size of the variable volume 24 of the pump 12 expands fluid therein and effects a flow of fluid from the fluid supply 56 into the variable volume 24 via the second check valve 62 and the second fluid channel 34. It will be appreciated that the first check valve 58 will not permit flow from the either the chamber 52 or the pressure indicator 54 to the variable volume 24 because of the orientation of the first check valve 58. Accordingly, reciprocating motion of piston 20 when the selector valve is oriented in the first position or orientation 50 draws fluid from the fluid supply 56 into the variable volume 24, compresses the fluid, and drives the fluid into the chamber 52 or the pressure indicator 54, thereby increasing the fluid pressure within the chamber 52 or the pressure indicator 54

Figure 2:
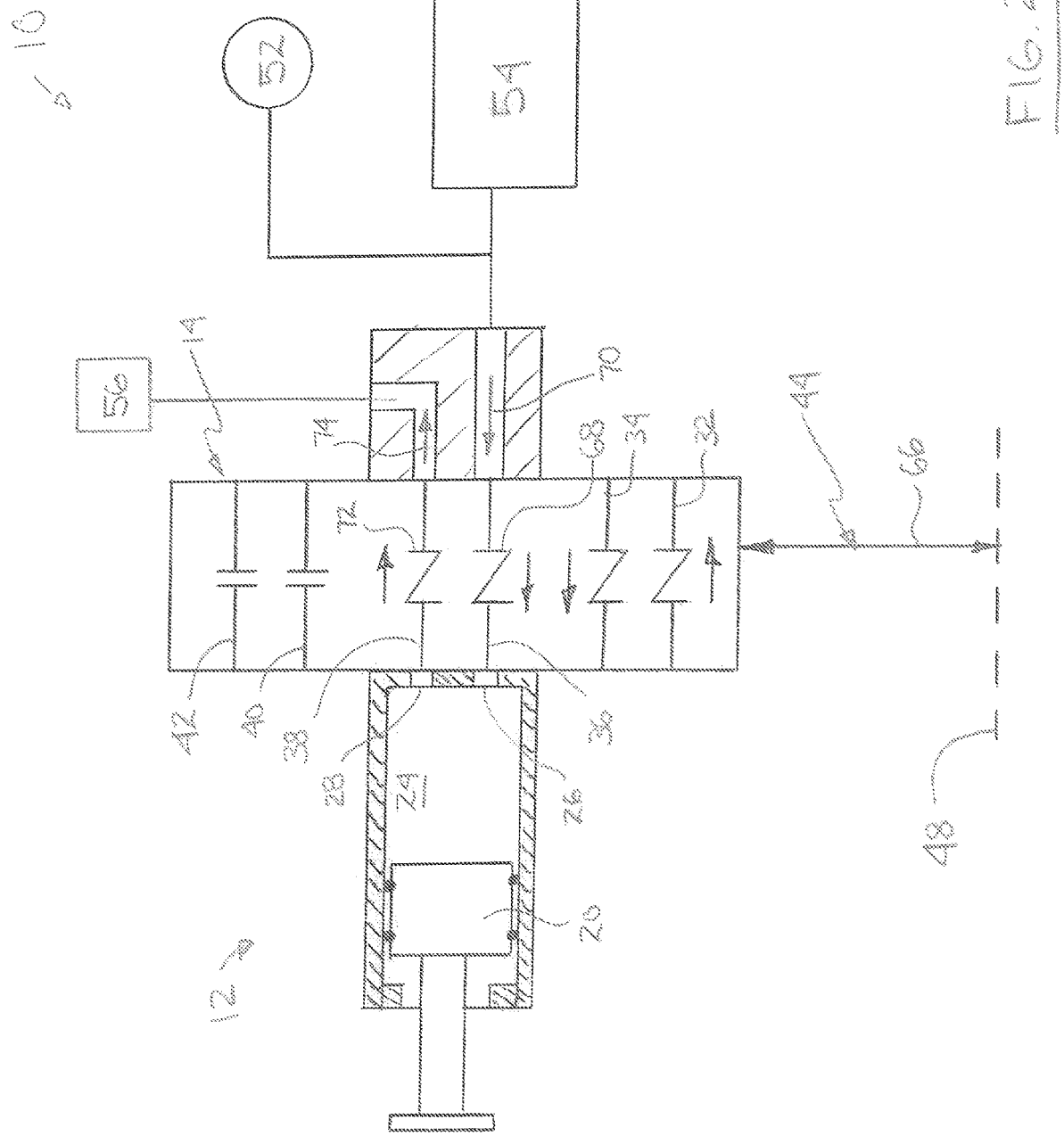
FIG. 2 presents a schematic view of another aspect of the pressure adjustment apparatus according to an embodiment of the present invention.

FIG. 2 presents a schematic view of another aspect of the pressure adjustment apparatus according to an embodiment of the present invention. In FIG. 2, the variable distance 44 between the selector valve 14 and the reference position 48 defines a second position or orientation 66 of the selector valve 14. When the selector valve 14 is oriented in the second position or orientation 66, the first aperture 26 of the pump body 16 is in fluid communication with the chamber 52, the pressure indicator 54, or combinations thereof, via the third fluid channel 36, and the second aperture 28 of the pump body 16 is in fluid communication with the fluid supply 56 via the fourth fluid channel 38.

According to an aspect of the present invention, a third check valve 68 is disposed in the third fluid channel 36 of the selector valve 14. The third check valve 68 may be oriented to permit flow through the third fluid channel 36 only in a flow direction 70 into the variable volume 24 of the pump 12. Further, a fourth check valve 72 may be disposed in the fourth fluid channel 38 of the selector valve 14. The fourth check valve 72 may be oriented to permit flow through the fourth fluid channel 38 only in a flow direction 74 out of the variable volume 24 of the pump 12. According to another aspect of the invention, when the selector valve is located in the second position or orientation 66, the variable volume 24 of the pump is not in fluid communication with any of the first fluid channel 32, the second fluid channel 34, the fifth fluid channel 40, or the sixth fluid channel 42.

When the selector valve 14 is oriented in the second position or orientation 66, increasing the size of the variable volume 24 of the pump 12 expands fluid therein and effects a flow of fluid from the third fluid channel 36 into the variable volume 24. The fluid flowing through the third fluid channel 36 may decrease a pressure within the chamber 52, the pressure indicator 54, or combinations thereof. It will be appreciated that the fourth check valve 72 will not permit flow from the fluid supply 56 to the variable volume 24 because of the orientation of the fourth check valve 72.

Further, when the selector valve 14 is oriented in the second position or orientation 66, decreasing the size of the variable volume 24 of the pump 12 compresses fluid therein and effects a flow of fluid from the variable volume 24 into the fluid supply 56 via the fourth check valve 72 and the fourth fluid channel 38. It will be appreciated that the third check valve 68 will not permit flow from the variable volume 24 into either the chamber 52 or the pressure indicator 54 because of the orientation of the third check valve 68. Accordingly, reciprocating motion of piston 20 when the selector valve is oriented in the second position or orientation 66 draws fluid from the chamber 52 or the pressure indicator 54, expands the fluid, and drives the fluid into the fluid supply 56, thereby decreasing the fluid pressure within the chamber 52 or the pressure indicator 54.

Figure 3:
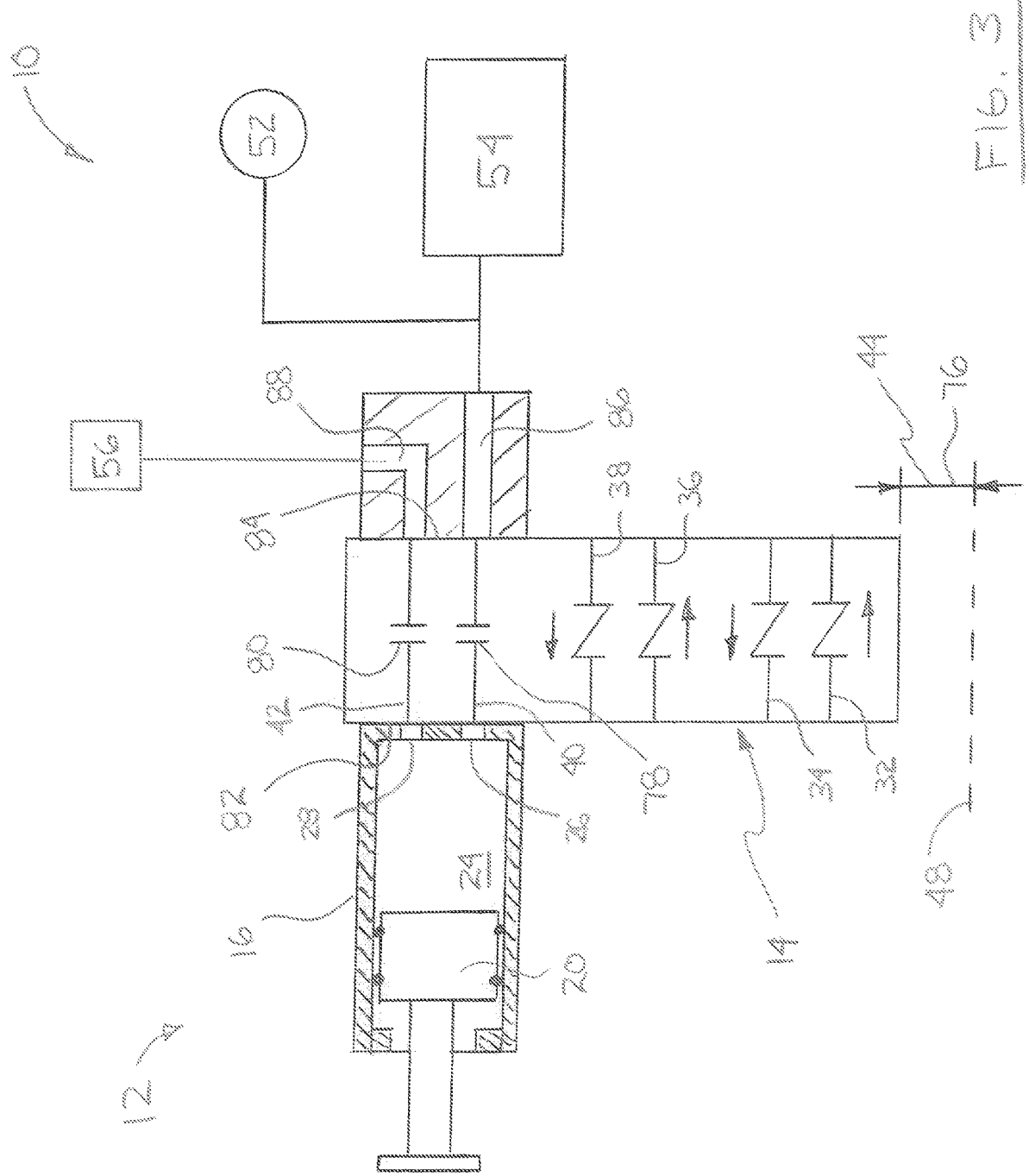
FIG. 3 presents a schematic view of yet another aspect of the pressure adjustment apparatus according to an embodiment of the present invention.

FIG. 3 presents a schematic view of yet another aspect of the pressure adjustment apparatus according to an embodiment of the present invention. In FIG. 3, the variable distance 44 between the selector valve 14 and the reference position 48 defines a third position or orientation 76 of the selector valve 14. When the selector valve 14 is oriented in the third position or orientation 76, the first aperture 26 of the pump body 16 is isolated from fluid communication with the chamber 52 or the pressure indicator 54 via the fifth fluid channel 40, and the second aperture 28 of the pump body 16 is isolated from fluid communication with the fluid supply 56 via the sixth fluid channel 42.

According to an aspect of the present invention, a first flow blockage 78 is disposed in the fifth fluid channel 40 of the selector valve 14, and a second flow blockage 80 is disposed in the sixth fluid channel 42. The first and second flow blockages 78, 80 could be formed by blind holes extending into the selector valve 14. Alternatively, the selector valve may not include either a fifth fluid channel 40 or a sixth fluid channel 42, but instead, have an external surface 82 that seals the first aperture 26 and the second aperture 28 of the pump body 16. Thus, when the selector valve 14 is in the third position or orientation 76, the variable volume 24 may be isolated from any fluid communication outside the pump 12 and the selector valve 14, or the variable volume 24 may be isolated from any fluid communication outside the pump 12.

According to another aspect of the present invention, an external surface 84 of the selector valve 14 may seal a fluid channel 86 extending between the selector valve 14 and the chamber 52, the pressure indicator 54, or both, and the external surface 84 of the selector valve 14 may seal a fluid channel 88 extending between the selector valve 14 and the fluid supply 56. According to yet another aspect of the invention, when the selector valve is located in the third position or orientation 76, the variable volume 24 of the pump is not in fluid communication with any of the first fluid channel 32, the second fluid channel 34, the third fluid channel 36, or the fourth fluid channel 38.

Although the first position 50, the second position 66, and the third position or orientation 76 of the selector valve 14 relative to the reference position 48 are shown in a single sequential order, it will be appreciated that the aforementioned selector valve positions 50, 66, 76 could be implemented in any sequential order with respect to the reference position 48.

Figure 4:
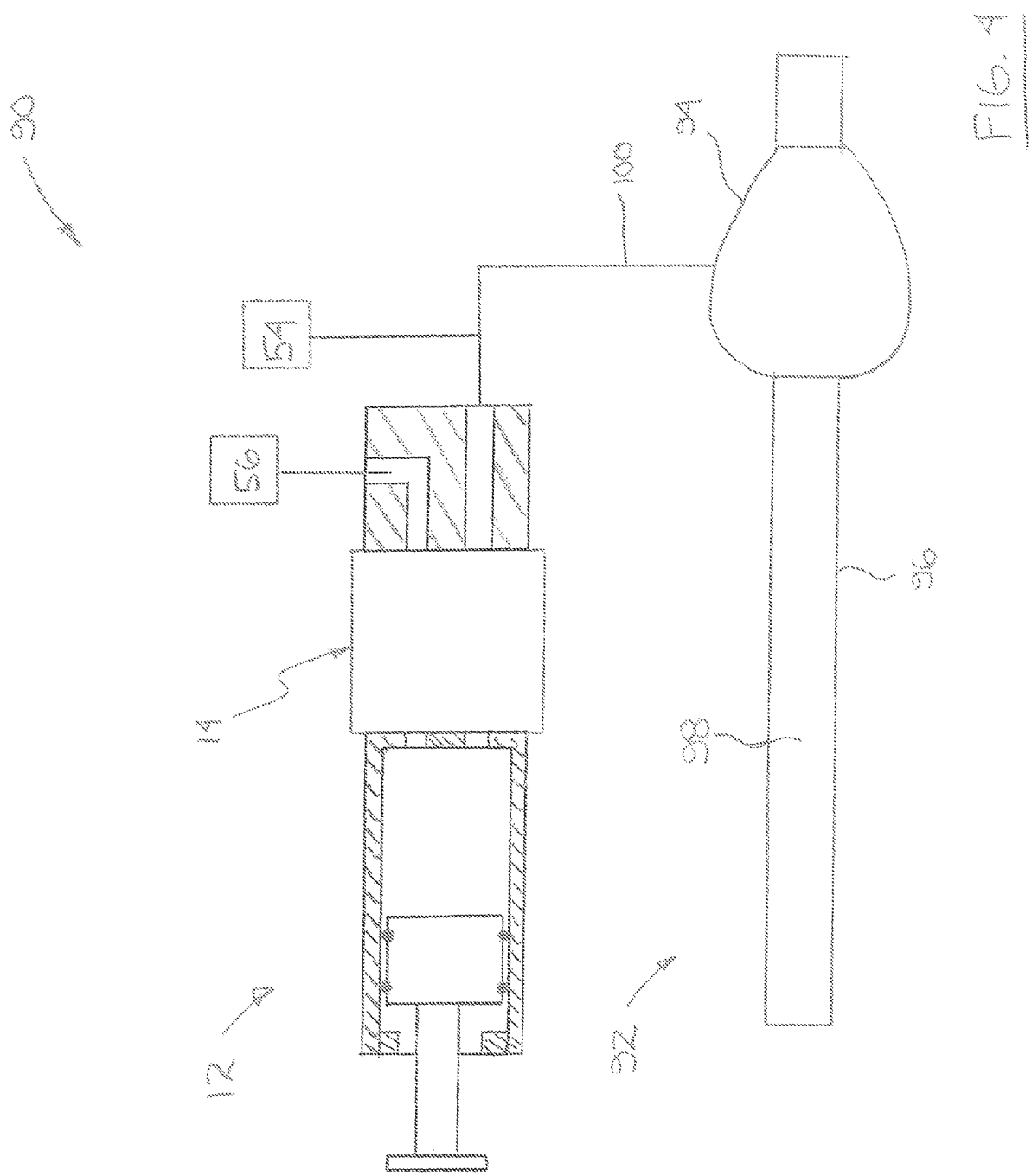
FIG. 4 presents a schematic view of an inflatable cuff system according to another embodiment of the present invention.

FIG. 4 presents a schematic view of an inflatable cuff system 90 according to another embodiment of the present invention. The inflatable cuff system 90 could be an endotracheal tube system, a tracheostomy tube system, an occlusion cuff system, or other inflatable cuff systems known to persons with ordinary skill in the art. The inflatable cuff system 90 includes a pump 12, a selector valve 14, and an inflatable cuff assembly 92.

The inflatable cuff assembly 92 includes an inflatable cuff 94 disposed around an outer periphery 96 of an elongated tube 98. In one embodiment, the inflatable cuff 94 and the elongated tube 98 define an annular volume therebetween. An internal volume of the inflatable cuff 94 is fluidly coupled to the selector valve 14 through a fluid supply channel 100. Optionally, the inflatable cuff system 90 may include a pressure indicator 54 fluidly coupled to the fluid supply channel 100.

As discussed above, regarding FIGS. 1-3, the pump 12 cooperates with the selector valve 14 to add or remove fluid from a chamber 52 fluidly coupled to the selector valve 14, or fluidly isolate the inflatable cuff 94 from the pump 12, the ambient environment, or both. In one aspect of the present invention, the pump 12 draws fluid from the fluid supply 56 and delivers the fluid to the inflatable cuff 94 through the fluid supply channel 100, thereby increasing a pressure within the inflatable cuff 94. In another aspect of the present invention, the pump 12 draws fluid away from inflatable cuff 94 through the fluid supply channel 100 and delivers the fluid to the fluid supply 56, thereby decreasing a pressure in the inflatable cuff. In yet another aspect of the present invention, the selector valve 14 fluidly isolates the inflatable cuff 94 from the pump 12, an ambient environment surrounding the inflatable cuff system 90, or both.

Figure 5:
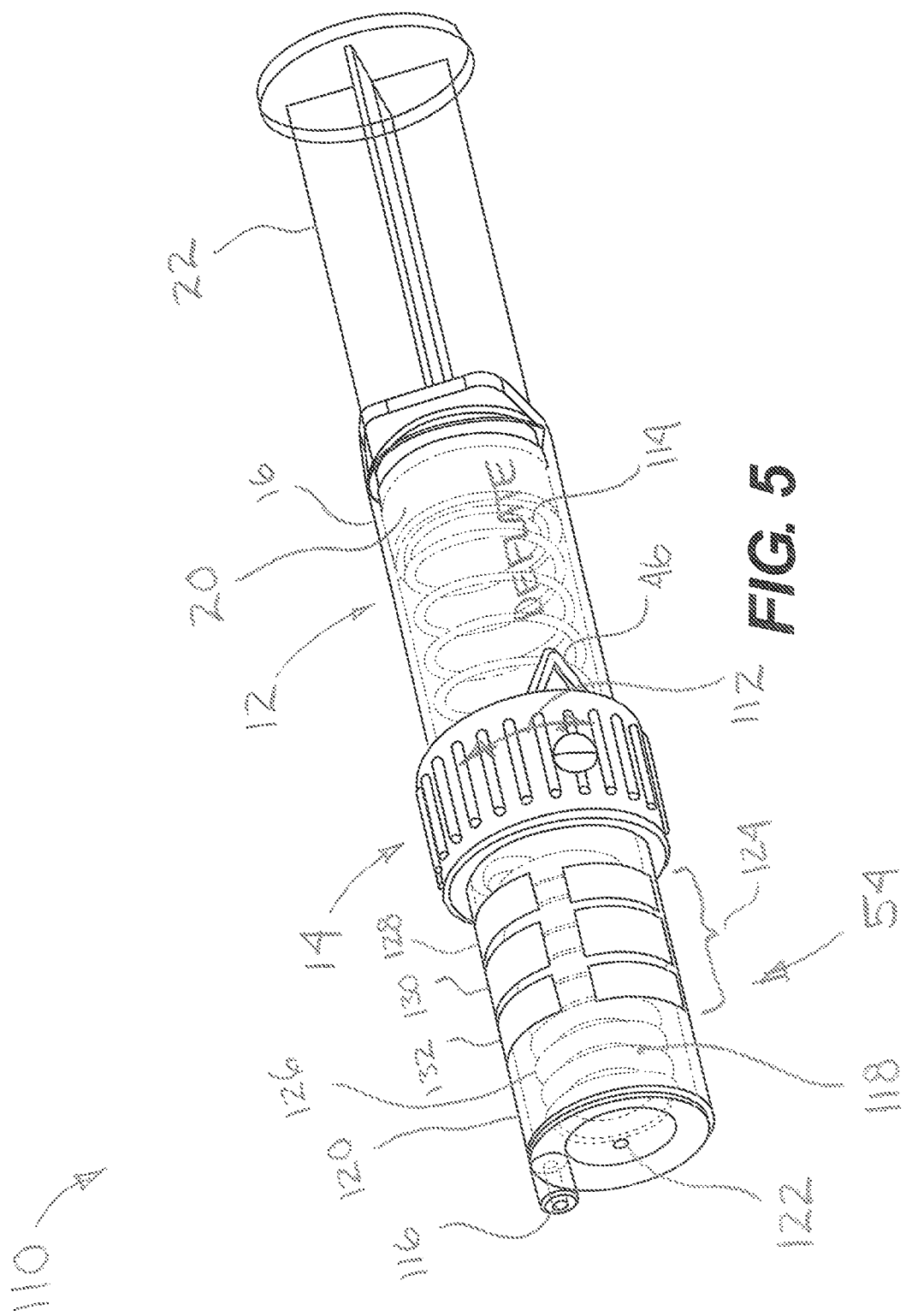
FIG. 5 presents a perspective view of a pressure adjustment apparatus according to yet another embodiment of the present invention.

FIG. 5 presents a perspective view of a pressure adjustment apparatus 110 according to yet another embodiment of the present invention. The pressure adjustment apparatus 110 includes a pump 12, a selector valve 14, and a pressure indicator 54. A piston stem or plunger 22 is attached to a piston or plunger head 20, which is disposed within the pump body 16. The selector valve 14 is fluidly coupled to the pump 12.

As shown in the non-limiting embodiment of FIG. 5, the selector valve 14 is rotatably coupled to the pump 12, such that rotation of the selector valve 14 in a circumferential direction 112 relative to the pump 12 enables switching between different modes of operation, as described above. The selector valve 14 may include a pointer 46 that may point to indicia 114 on the pump, where alignment of the pointer 46 and the indicia 114 is indicative of the operating mode of the pressure adjustment apparatus 110. The indicia 114 on the pump could include, for example, "Deflate," "Inflate," "Locked," "Sealed," combinations thereof, or other indicia that describe an operating mode of the pressure adjustment apparatus 110. Alternatively, it will be appreciated that the pointer 46 could be disposed on the pump 12 and the indicia 114 could be disposed on the selector valve 14.

When the pointer 46 is aligned with indicia 114 stating "Inflate," or the like, the pressure adjustment apparatus 110 may be configured to draw fluid from the fluid supply 56 (see FIG. 1) and deliver the fluid out of a port 116. The port 116 may be fluidly coupled to a chamber 52 (see FIG. 1) or an inflatable cuff 94 (see FIG. 4), for example. When the pointer 46 is aligned with indicia 114 stating "Deflate" or the like, for example, the pressure adjustment apparatus 110 may be configured to draw fluid from a chamber 52 (see FIG. 1), an inflatable cuff 94 (see FIG. 4), or the like, through the port 116 and deliver the fluid to a fluid supply 56 (see FIG. 1). When the pointer 46 is aligned with indicia 114 stating "Locked," "Sealed," or the like, the pressure adjustment apparatus 110 may be configured to fluidly isolate the pump 12 from fluid communication with the port 116, the pressure indicator 54, or both.

The pressure indicator 54 may be in fluid communication with both the selector valve 14 and the port 116. It will be appreciated that the pressure indicator 54 could indicate pressure based on various designs, such as, for example, a bellows-based design, a sliding piston-based design, a Bourdon tube design, an electrical strain gage-based design, a manometer-based design, or other pressure indicator designs known to persons having ordinary skill in the art.

In the non-limiting embodiment illustrated in FIG. 5, a bellows 118 is disposed within a housing 120. Either an internal surface or an external surface of the bellows 118 is in fluid communication with the selector valve 14. Whichever surface, internal or external, of the bellows 118 is not in fluid communication with the selector valve 14 is in fluid communication with a reference pressure source. In one aspect of the present invention, the pressure indicator is fluidly coupled to an ambient environment of the pressure indicator 54 through a vent orifice 122 through the housing 120, such that the reference pressure is an ambient pressure.

The pressure indicator 54 may include pressure indicia 124 disposed on the housing 120 and a reference point 126 coupled with motion of the bellows 118, such that a position of the reference point 126 relative to the pressure indicia 124 is indicative of a pressure at the port 116. It will be appreciated that the reference point 126 could be a longitudinal end of the bellows 118, a mark on one circumferential pleat of the bellows 118, a separate pointer fixed to the bellows 118, or other reference point mark known to persons with ordinary skill in the art. Further, at least a portion of the housing 120 may be permeable to visible light, such that a reference point 126 disposed within the housing 120 may be visible through the housing 120. Moreover, the pressure indicia 124 may also be permeable to visible light such that a reference point 126 disposed within the housing 120 may be visible through both the housing 120 and the pressure indicia 124.

The pressure indicia 124 may include a first indicia 128, a second indicia 130, and a third indicia 132. In one embodiment of the present invention, a pressure at the port 116 is low when the reference point 126 is aligned with the first indicia 128, a pressure at the port 116 is acceptable when the reference point 126 is aligned with the second indicia 130, and a pressure at the port 116 is high when the reference point 126 is aligned with the third indicia 132.

Figure 6:
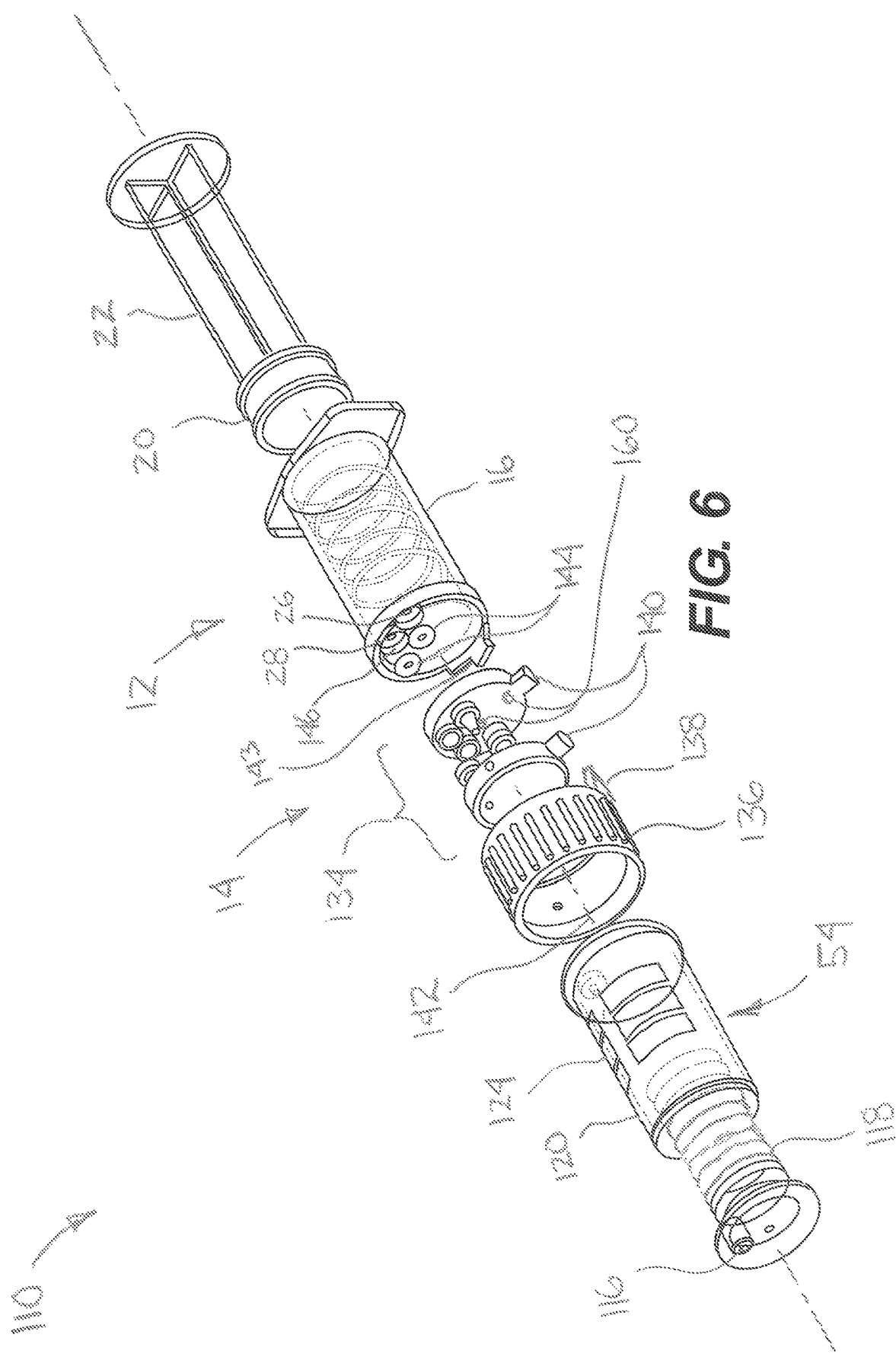
FIG. 6 presents an exploded view of the pressure adjustment apparatus illustrated in FIG. 5.
Figure 7:
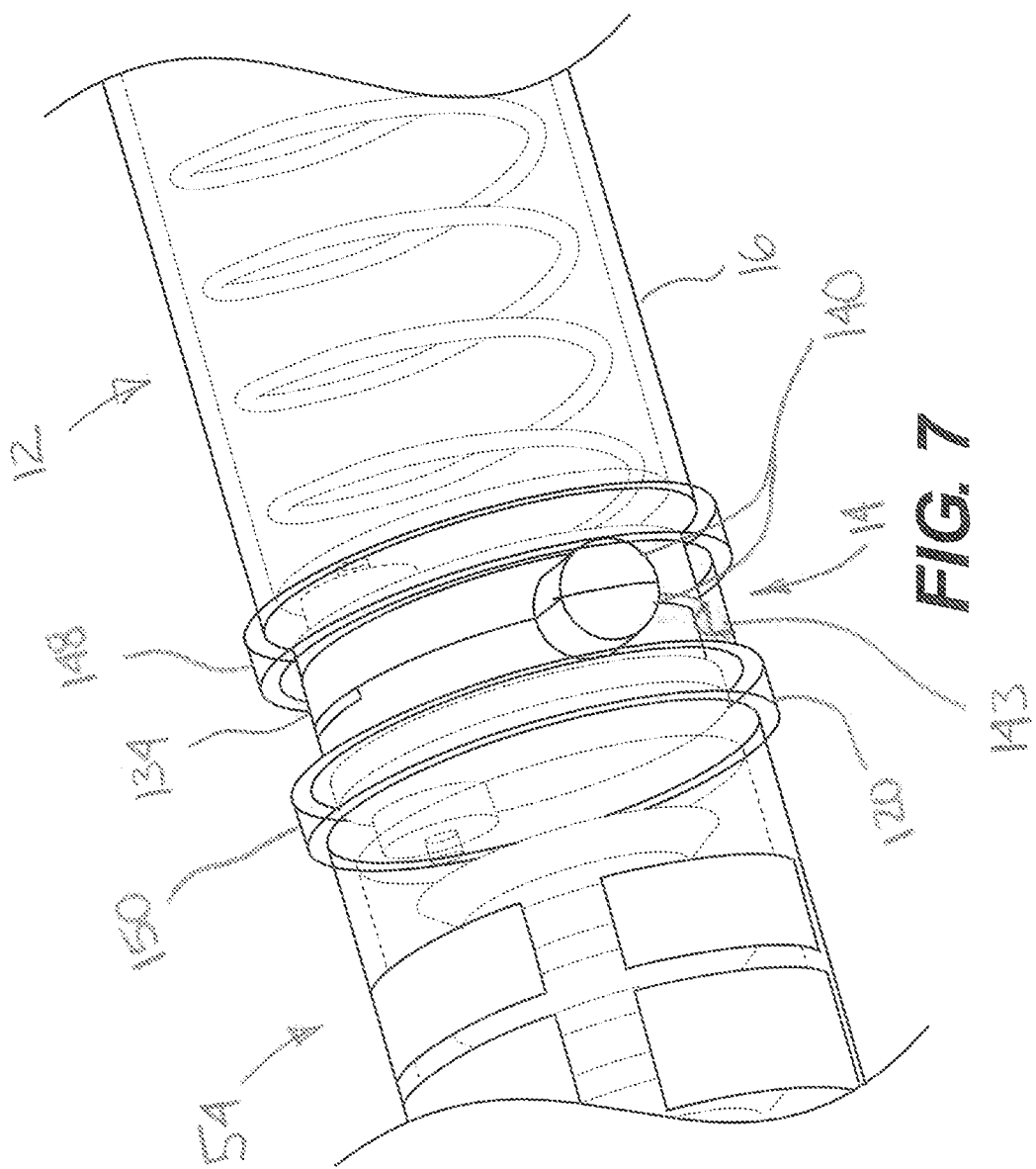
FIG. 7 shows a partial perspective view of the pressure adjustment apparatus illustrated in FIG. 5.

FIG. 6 presents an exploded view of the pressure adjustment apparatus illustrated in FIG. 5. The selector valve 14 includes a selector valve assembly 134 disposed between the pump body 16 and the housing 120 of the pressure indicator 54. A collar 136 may couple the housing 120 to the pump body 16, sandwiching the selector valve assembly 134 therebetween. FIG. 7 shows the selector valve assembly 134 sandwiched between the pump body and the housing 120 of the pressure indicator absent the collar 136.

The collar 136 may include a protrusion 138 extending therefrom. The protrusion 138 may operatively engage one or more tabs 140 in rotation to rotate the selector valve assembly 134 about an axis 142 of the selector valve 14. In one embodiment of the present invention, the protrusion 138 extends parallel to the axis 142, and the one or more tabs 140 extend in a radial direction that is normal to the axis 142. In another embodiment of the present invention the protrusion 138 also acts as the pointer 46. A projection 143 extending from the pump body 16 may limit a rotation of the selector valve 14 through interference with the one or more tabs 140 on the selector valve.

One or more seals 144 may be disposed between the pump body 16 and the selector valve 14. In one embodiment of the present invention, the one or more seals 144 are o-ring seals encircling the first aperture 26 through the pump body 16, the second aperture 28 through the pump body 16, or both. In another embodiment of the present invention, the one or more seals 144 are disposed within recesses 146 extending into the pump body 16 or the selector valve 14. Alternatively, a single-piece or multi-piece sheet gasket could be disposed between the pump body 16 and the selector valve 14 as a seal therebetween.

FIG. 7 shows a partial perspective view of the pressure adjustment apparatus illustrated in FIG. 5. In FIG. 7, one side of the selector valve assembly 134 abuts a flange 148 extending radially outward from the pump body 16, and another side of the selector valve assembly 134 abuts a flange 150 extending radially outward from the housing 120 of the pressure indicator 54. In one embodiment of the present invention the one or more tabs 140 are aligned in a circumferential direction about the selector valve 14 when the selector valve assembly 134 is assembled.

Figure 8:
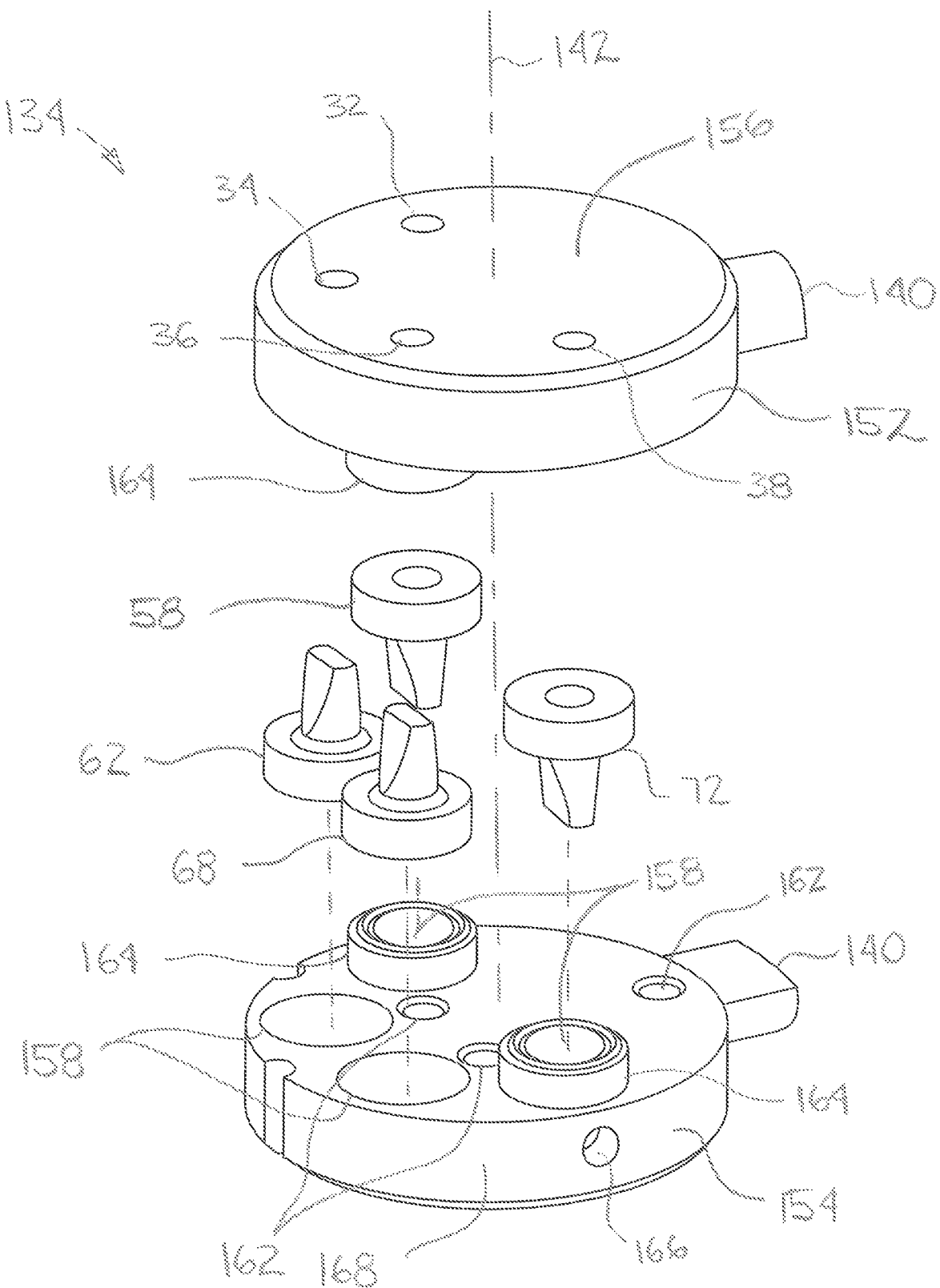
FIG. 8 shows an exploded view of a selector valve assembly according to still yet another embodiment of the present invention.

FIG. 8 shows an exploded view of a selector valve assembly 134 according to still yet another embodiment of the present invention. As shown in the embodiment illustrated in FIG. 8, the selector valve assembly 134 includes a first valve block 152 facing a second valve block 154. In one embodiment of the present invention, each of the first valve block 152 and the second valve block 154 have a substantially cylindrical shape. The first valve block 152 of the selector valve assembly defines a plurality of fluid channels therethrough, including: the first fluid channel 32, the second fluid channel 34, the third fluid channel, 36 and the fourth fluid channel 38.

The embodiment illustrated in FIG. 8 does not include a fifth fluid channel 40 or a sixth fluid channel 42. Instead, an outer planar surface 156 isolates the first aperture 26 and the second aperture 28 from fluid communication outside the selector valve 14, and the pump 12, when the outer planar surface 156 bears against the pump body 16 or seal 144 around the first aperture 26 and second aperture 28 of the pump 12.

The first check valve 58, the second check valve 62, the third check valve 68, and the fourth check valve 72 are disposed in the first fluid channel 32, the second fluid channel 34, the third fluid channel, 36 and the fourth fluid channel 38, respectively. The first check valve 58 and the fourth check valve 72 are oriented to allow flow in a first flow direction relative to the first valve block 152, and the second check valve 62 and the third check valve 68 are oriented to allow flow in a second flow direction relative to the first valve block 152, where the first flow direction is opposite the second flow direction. Any one of the check valves 58, 62, 68, 72 may be disposed in recesses 158 projecting into the first valve block 152 or the second valve block 154.

Pins 160 (see FIG. 6) projecting from a surface of the first valve block 152 may engage holes 162 (FIG. 8) projecting into a surface of the second valve block 154, such that rotational interference between the pins 160 and the holes 162 enable the first valve block 152 to rotate in unison with the second valve block 154. Further, annular rings 164 projecting from surfaces of the valve blocks 152, 154 and surrounding the check valves 58, 62, 68, 72 may engage corresponding recesses 158 on the opposite facing valve block 154, 152, such that the rotational interference between the annular rings 164 and the recesses 158 enable the first valve block 152 to rotate in unison with the second valve block 154.

The second valve block may include radial passages 166 extending from a circumferential face 168 of the second valve block to the fourth fluid channel 38, the second fluid channel 34 (not shown), or both. In turn, the second fluid channel 34 or the fourth fluid channel 38 may be in fluid communication with an ambient environment of the selector valve assembly 134 via the radial passages 166.

Although the pressure adjustment apparatus and methods are useful for adjusting and monitoring a pressure within a pressure cuff system, the apparatus and methods can also be used to adjust and monitor fluid pressure in other systems that could benefit from such adjustment and monitoring of fluid pressure.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. A pressure adjustment apparatus, comprising:
a pump including a pump body that defines a variable volume therein, the pump body further defining a first aperture and a second aperture therethrough, where the first aperture and the second aperture are located at a distal end of the pump body such that the first aperture and the second aperture of the pump body are in fluid communication with the variable volume;
a selector valve coupled to the pump and configured to move relative to the pump body, the selector valve defining a plurality of fluid channels therethrough, the selector valve including
a first check valve disposed in a first fluid channel of the plurality of fluid channels, the first check valve being oriented to permit flow through the first aperture and through the first fluid channel only in a first flow direction, the first flow direction being a flow direction out of the variable volume,
a second check valve disposed in a second fluid channel of the plurality of fluid channels, the second check valve being oriented to permit flow through the second aperture and through the second fluid channel only in a second flow direction, the second flow direction being a flow direction into the variable volume, and
a third check valve disposed in a third fluid channel of the plurality of fluid channels; the third check valve being oriented to permit flow through the first aperture and through the third fluid channel only in the second flow direction; and
a chamber in selective fluid communication with the pump through the selector valve,
wherein, when the selector valve is oriented in a first position relative to the pump, the first aperture of the pump body is in fluid communication with the first fluid channel of the selector valve, thereby permitting a flow from the variable volume of the pump into the chamber through the first fluid channel, and wherein, when the selector valve is oriented in a second position relative to the pump, the first aperture of the pump body is in fluid communication with the third fluid channel of the selector valve, thereby permitting a flow from the chamber into the variable volume of the pump through the third fluid channel, and wherein, when the selector valve is oriented in a third position relative to the pump, the first aperture through the pump body is blocked from fluid communication outside the pump.

2. The pressure adjustment apparatus of claim 1, wherein the selector valve further comprises a fourth check valve disposed in a fourth fluid channel of the plurality of fluid channels, the fourth check valve being oriented to permit flow through the second aperture and through the fourth fluid channel only in the first flow direction, wherein, when the selector valve is oriented in the first position relative to the pump, the second aperture of the pump body is in fluid communication with the second fluid channel of the selector valve, thereby permitting a flow from an external fluid reservoir or an ambient environment of the apparatus into the variable volume of the pump through the second fluid channel, and wherein, when the selector valve is oriented in the second position relative to the pump, the second aperture of the pump body is in fluid communication with the fourth fluid channel of the selector valve, thereby permitting a flow from the variable volume of the pump into the external fluid reservoir or the ambient environment of the apparatus through the fourth fluid channel.

3. The pressure adjustment apparatus of claim 2, wherein, when the selector valve is oriented in the third position relative to the pump, the first aperture through the pump body is further blocked from fluid communication outside the selector valve and the second aperture through the pump body is blocked from fluid communication outside the pump and the selector valve.

4. The pressure adjustment apparatus of claim 3, wherein, when the selector valve is oriented in the first position relative to the pump, the third fluid channel is in fluid communication with the pump, and wherein, when the selector valve is oriented in the second position relative to the pump, the first fluid channel is not in fluid communication with the pump.

5. The pressure adjustment apparatus of claim 4, wherein, when the selector valve is oriented in the first position relative to the pump, the fourth fluid channel is not in fluid communication with the pump, and wherein, when the selector valve is oriented in the second position relative to the pump, the second fluid channel is not n fluid communication with the pump.

6. The pressure adjustment apparatus of claim 1, wherein the chamber is an inflatable cuff.

7. The pressure adjustment apparatus of claim 1, wherein the selector valve is rotatable about an axis of the selector valve with respect to the pump.

8. The pressure adjustment apparatus of claim 7, wherein the axis of the selector valve is substantially coaxial with a longitudinal axis of the variable volume of the pump.

9. The pressure adjustment apparatus of claim 1, wherein the chamber is also in fluid communication with a pressure indicator.

10. The pressure adjustment apparatus of claim 9, wherein the pressure indicator includes a bellows in fluid communication with the chamber.

11. The pressure adjustment apparatus of claim 10, wherein an internal surface of the bellows is in fluid communication with the chamber.

12. The pressure adjustment apparatus of claim 10, wherein an external surface of the bellows is in fluid communication with the chamber.

13. The pressure adjustment apparatus of claim 1, wherein, when the selector valve is oriented in the third position relative to the pump, the second aperture through the pump body is blocked from fluid communication outside the pump.

14. An inflatable cuff system, comprising:
a tube defining a lumen therein;
a pump including a pump body that defines a variable volume therein, the pump body further defining a first aperture and a second aperture therethrough, where the first aperture and the second aperture are located at a distal end of the pump body such that the first aperture and the second aperture of the pump body are in fluid communication with the variable volume;
a selector valve coupled to the pump and the tube, the selector valve being configured to move relative to the pump body and defining a plurality of fluid channels therethrough, the selector valve including
a first check valve disposed in a first fluid channel of the plurality of fluid channels, the first check valve being oriented to permit flow through the first aperture and through the first fluid channel only in a first flow direction, the first flow direction being a flow direction out of the variable volume,
a second check valve disposed in a second fluid channel of the plurality of fluid channels, the second check valve being oriented to permit flow through the second aperture and through the second fluid channel only in a second flow direction, the second flow direction being a flow direction into the variable volume, and
a third check valve disposed in a third fluid channel of the plurality of fluid channels, the third check valve being oriented to permit flow through the first aperture and through the third fluid channel only in the second flow direction; and
an inflatable cuff in fluid communication with the pump via the selector valve and the lumen,
wherein, when the selector valve is oriented in a first position relative to the pump, the first aperture of the pump body is in fluid communication with the first fluid channel of the selector valve, thereby permitting a flow from the variable volume of the pump into the inflatable cuff through the first fluid channel, and
wherein, when the selector valve is oriented in a second position relative to the pump, the first aperture of the pump body is in fluid communication with the third fluid channel of the selector valve, thereby permitting a flow from the inflatable cuff into the variable volume of the pump through the third fluid channel, and
wherein, when the selector valve is oriented in a third position relative to the pump, the first aperture through the pump body is blocked from fluid communication outside the pump.

15. The inflatable cuff system of claim 14, wherein the selector valve further comprises
a fourth check valve disposed in a fourth fluid channel of the plurality of fluid channels, the fourth check valve being oriented to permit flow through the second aperture and through the fourth fluid channel only in the first flow direction,
wherein, when the selector valve is oriented in the first position relative to the pump, the second aperture of the pump body is in fluid communication with the second fluid channel of the selector valve, thereby permitting a flow from an external fluid reservoir or an ambient environment of the apparatus into the variable volume of the pump through the second fluid channel, and
wherein, when the selector valve is oriented in the second position relative to the pump, the second aperture of the pump body is in fluid communication with the fourth fluid channel of the selector valve, thereby permitting a flow from the variable volume of the pump into the external fluid reservoir or the ambient environment of the apparatus through the fourth fluid channel.

16. The inflatable cuff system of claim 14, wherein, when the selector valve is oriented in the third position relative to the pump, the first aperture through the pump body is further blocked from fluid communication outside the selector valve and the second aperture through the pump body is blocked from fluid communication outside the pump and the selector valve.

17. The inflatable cuff system of claim 14, wherein, when the selector valve is oriented in the third position relative to the pump, the second aperture through the pump body is blocked from fluid communication outside the pump.

18. A pressure adjustment apparatus, comprising:
a pump including a pump body that defines a variable volume therein, the pump body further defining a first aperture located at a distal end of the pump body and a second aperture located at a distal end of the pump body, the first and second apertures being in fluid communication with the variable volume;
a selector valve coupled to the pump and configured to move relative to the pump body, the selector valve defining a plurality of fluid channels therethrough, the selector valve including a first check valve disposed in a first fluid channel of the plurality of fluid channels and being oriented to permit flow out of the variable volume through the first aperture, a second check valve disposed in a second fluid channel of the plurality of fluid channels and being oriented to permit flow into the variable volume through the second aperture, and a third check valve disposed in a third fluid channel of the plurality of fluid channels and being oriented to permit flow into the variable volume through the first aperture; and
a chamber in selective fluid communication with the pump through the selector valve,
wherein the first aperture of the pump body is in fluid communication with first fluid channel of the selector valve when the selector valve is oriented in a first position relative to the pump, thereby permitting a flow from the variable volume of the pump into the chamber through the first fluid channel, and
wherein the first aperture of the pump body is in fluid communication with the third fluid channel of the selector valve when the selector valve is oriented in a second position relative to the pump, thereby permitting a flow from the chamber into the variable volume of the pump through the third fluid channel.

19. The pressure adjustment apparatus of claim 18, wherein the selector valve further comprises a fourth check valve disposed in a fourth fluid channel of the plurality of fluid channels, the fourth check valve being oriented to permit flow out of the variable volume through the second aperture,
wherein the second aperture of the pump body is in fluid communication with the second fluid channel of the selector valve when the selector valve is oriented in the first position relative to the pump, thereby permitting a flow from an external fluid reservoir or an ambient environment of the apparatus into the variable volume of the pump through the second fluid channel, and
wherein the second aperture of the pump body is in fluid communication with the fourth fluid channel of the selector valve when the selector valve is oriented in the second position relative to the pump, thereby permitting a flow from the variable volume of the pump into the external fluid reservoir or the ambient environment of the apparatus through the fourth fluid channel.

20. The pressure adjustment apparatus of claim 19,
wherein the third fluid channel is not in fluid communication with the pump and the fourth fluid channel is not in fluid communication with the pump when the selector valve is oriented in the first position relative to the pump,
wherein the first fluid channel is not in fluid communication with the pump and the second fluid channel is not in fluid communication with the pump when the selector valve is oriented in the second position relative to the pump, and
wherein the first aperture through the pump body is blocked from fluid communication outside the selector valve and the second aperture through the pump body is blocked from fluid communication outside the pump and the selector valve when the selector valve is oriented in a third position relative to the pump.

* * * * *